United States Patent
Simon

(10) Patent No.: US 7,847,037 B2
(45) Date of Patent: Dec. 7, 2010

(54) PROCESS FOR PREPARING A CATALYST CONTAINING A MODIFIED ZEOLITE AND ITS USE IN OLIGOMERIZATION OF LIGHT OLEFINS

(75) Inventor: Laurent Simon, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 0 days.

(21) Appl. No.: 12/158,225

(22) PCT Filed: Nov. 3, 2006

(86) PCT No.: PCT/FR2006/002466

§ 371 (c)(1),
(2), (4) Date: Oct. 20, 2008

(87) PCT Pub. No.: WO2007/080240

PCT Pub. Date: Jul. 19, 2007

(65) Prior Publication Data

US 2009/0240008 A1 Sep. 24, 2009

(30) Foreign Application Priority Data

Dec. 20, 2005 (FR) .................................. 05 13209

(51) Int. Cl.
*C08F 4/72* (2006.01)
(52) U.S. Cl. ...................... 526/108; 502/152
(58) Field of Classification Search ................ 502/152, 502/943; 526/108
See application file for complete search history.

(56) References Cited

U.S. PATENT DOCUMENTS

| 4,542,251 A | 9/1985 | Miller et al. |
| 4,868,146 A | 9/1989 | Chu et al. |
| 5,349,113 A | 9/1994 | Chang et al. |
| 6,051,519 A | 4/2000 | Wu et al. |
| 2002/0091293 A1 | 7/2002 | Chang et al. |
| 2003/0055305 A1 | 3/2003 | Beck et al. |
| 2008/0021253 A1 | 1/2008 | Corma Canos et al. |

FOREIGN PATENT DOCUMENTS

| WO | WO 2004/108282 A3 | 12/2004 |
| WO | WO 2005/118515 A1 | 12/2005 |

*Primary Examiner*—Ling-Siu Choi
*Assistant Examiner*—Sonya Wright
(74) *Attorney, Agent, or Firm*—Millen, White, Zelano & Branigan, P.C.

(57) ABSTRACT

A process for the preparation of a catalyst that contains at least one modified zeolite, whereby said zeolite—before being modified—has a maximum pore opening diameter that is less than or equal to 7 Å, and whereby said process comprises at least:

a) One stage for introducing at least one metal that is selected from among the metals of groups VIB and VIII of the periodic table on a substrate that is based on at least one protonated zeolite,
b) One stage for treating said zeolite in the presence of at least one molecular compound that contains at least one silicon atom, and said compound that has a diameter that is greater than the maximum opening diameter of the pores of said zeolite,
c) At least one heat treatment stage, is described.

12 Claims, No Drawings

PROCESS FOR PREPARING A CATALYST CONTAINING A MODIFIED ZEOLITE AND ITS USE IN OLIGOMERIZATION OF LIGHT OLEFINS

TECHNICAL FIELD

This invention relates to a process for preparation of a catalyst that is based on a modified zeolite that has small and/or medium-sized pores, i.e., that has a maximum pore opening diameter that is less than or equal to 7 Å, so as to obtain a catalyst that is advantageously used in various processes for chemical conversion of hydrocarbons. More particularly, the invention also relates to the use of said catalyst that contains said modified zeolite in a process for oligomerization of a light olefinic feedstock.

PRIOR ART

The use of zeolites with shape selectivity such as the ZSM-5 zeolite for the oligomerization reaction of olefins has been known for a long time. The Mobil olefin oligomerization process developed in the 1980s, described, i.a., in the U.S. Pat. No. 4,150,062 and U.S. Pat. No. 4,227,992, uses a ZSM-5-type zeolite for the conversion of butenes into oligomers. The products that are obtained have a very low degree of branching and make good-quality jet fuel and diesel fractions. Whereby this process provides very low diesel fraction yield (fraction obtained after distillation of the oligomerate between 200° C.-360° C.), it is used primarily for producing jet fuel.

Several patents have already noted methods for modifying zeolites. In particular, the U.S. Pat. No. 4,402,867 describes a method for preparation of a zeolite-based catalyst that comprises a stage that consists in depositing in aqueous phase at least 0.3% by weight of amorphous silica inside the pores of the zeolite. The U.S. Pat. No. 4,996,034 describes a process for substituting aluminum atoms that are present in a zeolitic framework by silicon atoms, whereby said process is carried out in an aqueous medium stage using fluorosilicate salts. The U.S. Pat. No. 4,451,572 describes the preparation of a zeolitic catalyst that comprises a stage for depositing organosilicic materials in vapor or liquid phase, whereby the zeolites in question are large-pore zeolites, in particular the Y zeolite.

The U.S. Pat. No. 5,057,640 describes a process for oligomerization of the propylene that uses a catalyst that contains a zeolite with an Si/Al ratio of more than 12 and a constraint index (CI) of between 1 and 12 and in which at least 0.1% by weight of silica relative to the weight of the zeolite has been added. The catalyst in question in this U.S. Pat. No. 5,057,640 has an n-hexane adsorption that is 1% less than in the initial material.

SUMMARY

This invention relates to a process for preparation of a catalyst that contains at least one modified zeolite, whereby said zeolite—before being modified—has a maximum pore opening diameter that is less than or equal to 7 Å, whereby said process comprises at least:

a) One stage for introducing at least one metal that is selected from among the metals of groups VIB and VIII of the periodic table on a substrate that is based on at least one protonated zeolite, b) One stage for treating said zeolite in the presence of at least one molecular compound that contains at least one silicon atom, and said compound that has a diameter that is greater than the maximum opening diameter of the pores of said zeolite is deposited on the outside surface of said zeolite in gaseous phase, c) At least one heat treatment stage.

Said zeolite is preferably selected from among the zeolites of structural type MEL, MFI, ITH, NES, EUO, ERI, FER, CHA, MFS, MWW, MTT, TON and MOR.

This invention also relates to the use of said catalyst in a process for oligomerization of an olefinic feedstock that contains hydrocarbon molecules that have 2 to 12 carbon atoms per molecule.

ADVANTAGE

It was discovered, surprisingly enough, that a catalyst that comprises a modified zeolite—prepared according to a process that comprises at least a) one stage for introducing at least one metal that is selected from among the metals of groups VIB and VIII of the periodic table on a substrate that is based on at least one protonated zeolite, b) one stage for treating said zeolite in the presence of at least one molecular compound that contains at least one silicon atom, said compound having a diameter that is greater than the maximum opening diameter of the pores of said zeolite, c) at least one heat treatment stage—leads to improved catalytic performances, in particular in terms of yield and selectivity of the diesel fraction in a reaction for oligomerization of an olefinic feedstock that contains hydrocarbon molecules that have 2 to 12 carbon atoms per molecule, preferably 3 to 7 carbon atoms per molecule, and very preferably that contain 4 to 6 carbon atoms per molecule.

In particular, such a catalyst makes it possible to increase in particular the yield of the diesel fraction relative to the one that is obtained by employing a catalyst of the prior art. The cetane number that reflects the linearity of the hydrocarbon chains that are present in the diesel fraction and that represents the quality of the diesel fraction is also advantageously improved relative to the one that a diesel fraction that is obtained by this reaction generally has. The use of the catalyst as described above in a process for oligomerization of an olefinic feedstock that contains hydrocarbon molecules that have 2 to 12 carbon atoms per molecule, preferably 3 to 7 carbon atoms per molecule, and very preferably that contains 4 to 6 carbon atoms per molecules, makes possible the production of an oligomerate of very good quality, which advantageously after distillation to the suitable fraction point can be integrated with the diesel pool of a refinery.

DESCRIPTION OF THE INVENTION

This invention has as its object a process for preparation of a catalyst that contains at least one modified zeolite, whereby said zeolite—before being modified—has a maximum pore opening diameter that is less than or equal to 7 Å, whereby said process comprises at least:

a) One stage for introducing at least one metal that is selected from among the metals of groups VIB and VIII of the periodic table on a substrate that is based on at least one protonated zeolite, b) A stage for treating said zeolite in the presence of at least one molecular compound that contains at least one silicon atom, and said compound that has a diameter that is greater than the maximum opening diameter of the pores of said zeolite is deposited on the outside surface of said zeolite in gaseous phase, c) At least one heat treatment stage.

According to the invention, the initial zeolite, not having yet been modified in order to be contained in the catalyst that is prepared according to the process of the invention, has a maximum pore opening diameter that is less than or equal to 7 Å and preferably less than 6.5 Å. Said zeolite is selected from among the zeolites that are defined in the classification "Atlas of Zeolite Structure Types," W. M. Meier, D. H. Olson and Ch. Baerlocher, 5$^{th}$ Revised Edition, 2001, Elsevier" to which this application also refers, but it can also be any zeolite that has a maximum pore opening diameter that is less than or equal to 7 Å. The zeolites that are listed in the "Atlas of Zeolite Structure Types" are classified there according to their structural type. All of the zeolites that have a maximum pore opening diameter that is less than or equal to 7 Å, and preferably less than 6.5 Å, are suitable for the implementation of the process for preparation according to the invention and in particular for the implementation of the stage for treatment b) of the process according to the invention. According to the invention, the maximum pore opening diameter of a zeolite corresponds to the maximum size of the pore openings ("ring dimensions") mentioned in the "Atlas of Zeolite Structure Types" for each of the structural types. Advantageously, the zeolite that is initially used, before being modified in order to be contained in the catalyst that is prepared according to the process of the invention, has either one or more channels whose opening is defined by a ring with 10 oxygen atoms (10 MR) or one or more channels whose opening is defined by a ring with 12 oxygen atoms (12 MR) or else at the same time one or more channels whose opening is defined by a ring with 8 oxygen atoms (8 MR), and one or more channels whose opening is defined by a ring with 10 oxygen atoms (10 MR), or else at the same time one or more channels whose opening is defined by a ring with 8 oxygen atoms (8 MR) and one or more channels whose opening is defined by a ring with 12 oxygen atoms (12 MR), or else at the same time one or more channels whose opening is defined by a ring with 8 oxygen atoms (8 MR) and one or more channels whose opening is defined by a ring with 10 oxygen atoms (10 MR) and one or more channels whose opening is defined by a ring with 12 oxygen atoms (12 MR), whereby said channels can be interconnected. One zeolite that has at least several channels whose opening is defined by a ring with 12 oxygen atoms (12 MR) is particularly suitable for the implementation of the process for preparation of the catalyst according to the invention as soon as it has a maximum pore opening diameter that is less than or equal to 7 Å. In particular, a MOR-structural-type zeolite, which at the same time has channels whose opening is defined by a ring with 8 oxygen atoms (8 MR) and channels whose opening is defined by a ring with 12 oxygen atoms (12 MR), is suitable for the implementation of the process for preparation according to the invention. The MOR-structural-type zeolites have a maximum pore opening diameter of 7.0 Å.

The zeolite, modified according to the different stages of the process according to the invention, initially contains, i.e., before being modified, at least silicon and aluminum in a proportion such that the Si/Al atomic ratio is preferably between 2 and 200, more preferably between 5 and 100, and even more preferably between 8 and 80. It advantageously contains at least one other element W, different from silicon and aluminum, being integrated in tetrahedral form in the framework of the zeolite. Preferably, said element W is selected from among iron, germanium, boron and titanium and represents a portion by weight of between 5 and 30% of all of the atoms that constitute the zeolitic framework, except for the oxygen atoms. The zeolite then has an (Si+W)/Al ratio of between 2 and 200, preferably between 5 and 100, and very preferably between 8 and 80, whereby W is defined as above.

The zeolite that is modified according to the various stages of the process according to the invention is preferably selected from among the zeolites of structural type MEL, MFI, ITH, NES, EUO, ERI, FER, CHA, MFS, MWW, MTT, TON and MOR and very preferably selected from among the zeolites of structural type MFI, MOR and FER. Among the MEL-structural-type zeolites, the ZSM-11 zeolite is preferred. Among the MFI-structural-type zeolites, the ZSM-5 zeolite is preferred. Among the ITH-structural-type zeolites, the ITQ-13 zeolite is preferred (U.S. Pat. No. 6,471,941). Among the NES-structural-type zeolites, the NU-87 zeolite is preferred. Among the EUO-structural-type zeolites, the EU-1 zeolite is preferred. Among the ERI-structural-type zeolites, the erionite zeolite is preferred. Among the FER-structural-type zeolites, the ferrierite and ZSM-35 zeolites are preferred. Among the CHA-structural-type zeolites, the chabazite zeolite is preferred. Among the MFS-structural-type zeolites, the ZSM-57 zeolite is preferred. Among the MWW-structural-type zeolites, the MCM-22 zeolite is preferred. Among the MTT-structural-type zeolites, the ZSM-23 zeolite is preferred. Among the TON-structural-type zeolites, the ZSM-22 zeolite is preferred. Among the MOR-structural-type zeolites, the mordenite zeolite is preferred. These zeolites and their method of preparation are well known to one skilled in the art.

According to the invention, the first stage of the process for preparation of the catalyst according to the invention is either stage a) or stage b). Stage b), whether it is carried out before or after stage a), is preferably followed immediately by stage c).

The zeolite that is used for the implementation of the first stage of the process for preparation of the catalyst according to the invention—i.e., used for the implementation of stage a) that is carried out in the presence of at least one metal of groups VIB and/or VIII of the periodic table or for the implementation of stage b) that is carried out in the presence of at least one molecular compound that contains at least one silicon atom that has a well-defined diameter—comes in calcined form and contains at least one proton such that it is found in its protonated form (hydrogen H$^+$ form) in which the cation content, except for H$^+$, is less than 30% of the total number of cations, preferably less than 20% and very preferably less than 15% relative to the total number of cations on the zeolite. In the case where, prior to the implementation of the first stage of the process for preparation of the catalyst according to the invention (stage a) or stage b)), the zeolite that is to be modified is in its crude synthesis form, still containing the organic structuring agent that is used to prepare it, it is possible to initiate a calcination of said zeolite at a temperature of between 300 and 700° C., preferably between 400 and 600° C.; then, if the zeolite contains one or more alkaline/alkaline-earth metal(s), one or more ionic exchange(s) will be initiated by a solution that contains at least one ammonium salt, for example ammonium nitrate NH$_4$NO$_3$, in such a way as to eliminate at least partially, preferably virtually totally, an alkaline cation that is present in the zeolite. A stage of calcination under a dry air flow, at a temperature that is generally between about 400 and 500° C., then has as its object to generate the formation of the protons in the zeolite by desorption of ammonia, thus leading to the hydrogen form of the zeolite, ready for the implementation of the first stage of the process for preparation according to the invention.

The zeolite that is used for the implementation of the first stage of the process for preparation of the catalyst according to the invention is an acid zeolite that contains between 70 and 100%, preferably between 80 and 100%, and very preferably between 85 and 100% of compensation cations of protonic form $H^+$, whereby the remainder of the cations is selected preferably from among the metals of groups IA and IIA of the periodic table, and more particularly said cation is selected from among the cations $Na^+$, $Li^+$, $K^+$, $Rb^+$, $Cs^+$, $Ba^{2+}$, and $Ca^{2+}$.

Stage a) of the process for preparation of the catalyst according to the invention is a stage for introducing at least one metal that is selected from among the metals of groups VIB and VIII of the periodic table on a substrate that is based on at least one protonated zeolite. Preferably, said metal that is selected from among the metals of groups VIB and VIII of the periodic table is selected from among nickel, iron, palladium, ruthenium and chromium, very preferably from among nickel and chromium. Very advantageously, the metal of group VIII is nickel. Among the metals of group VIB, chromium is preferred. For the preparation of the catalyst according to the invention, the deposition of at least one metal that is selected from among the metals of groups VIB and VIII is generally carried out by dry impregnation, by impregnation by excess or by ionic exchange(s) according to methods that are well known to one skilled in the art, preferably by ionic exchange(s). Regarding the introduction by ionic exchange of nickel, it is preferred to use an aqueous solution that contains nickel under the degree of oxidation +2, for example nickel sulfate. The content by weight of the metal that is selected from the groups VIB and VIII, introduced on the zeolitic substrate, is advantageously between 0.01 and 10% by weight, and preferably between 0.1 and 5% by weight relative to the weight of the catalyst that is prepared according to the process of the invention. According to a first implementation of stage a) of the process of the invention, the substrate that is based on at least one protonated zeolite consists entirely of said protonated zeolite, which in terms of maximum opening diameter of the pores, structure and chemical composition, has the characteristics that are described above. According to a second implementation of stage a) of the process of the invention, the substrate that is based on at least one protonated zeolite consists of said protonated zeolite that is shaped with a matrix and optionally a binder.

The process for preparation of the catalyst according to the invention comprises a stage b) for selecting the zeolite, coming in its protonated form, whereby said selection stage can be carried out either before the stage of introducing at least one metal of groups VIB and/or VIII according to said stage a) or after said stage a). In terms of this invention, "selection" is defined as the neutralization of the acidity of the outside surface of each of the crystals of the zeolite. The neutralization of the acidity can be done by any method that is known to one skilled in the art. To carry out the specific selection of the acid sites of the outside surface of the zeolites, the conventional methods generally use molecules whose kinetic diameter is greater than the diameter of the opening of the pores of the zeolite. More specifically, stage b) for selection consists in treating the zeolite, coming in its protonated form, optionally subjected in advance to said stage a), in the presence of at least one molecular compound that contains at least one silicon atom, whose diameter is greater than the maximum opening diameter of the pores of the zeolite that is to be treated according to stage b). Preferably, the process for preparation of the catalyst according to the invention comprises only a single stage b).

The molecules that are generally used to passivate or select the outside surface of the zeolite are compounds that contain atoms that can interact with the outside surface sites of each of the crystals of the zeolite. The molecules that are used according to the invention are organic or inorganic molecules that contain one or more silicon atom(s). Also, according to stage b) for treatment of the process according to the invention, the protonated zeolite, optionally subjected in advance to said stage a), is subjected to a stage for treatment in the presence of at least one molecular compound that contains at least one silicon atom. Said stage b) makes possible the deposition of a layer of said molecular compound that contains at least one silicon atom on the outside surface of the zeolite that will be transformed after stage c) into a layer of amorphous silica on the outside surface of each of the crystals of the zeolite. Preferably, the molecular compound that contains at least one silicon atom is selected from among the compounds of formula $Si-R_4$ and $Si_2-R_6$, where R may be either hydrogen or an alkyl, aryl or acyl group, or an alkoxy (O—R') group, or a hydroxyl (—OH) group, or else a halogen, preferably an alkoxy (O—R') group. Within the same molecule $Si-R_4$ or $Si_2-R_6$, the group R may be either identical or different. For example, according to the formulas that are described above, it may be possible to select molecular compounds of formula $Si_2H_6$ or $Si(C_2H_5)_3(CH_3)$. Thus, the molecular compound that contains at least one silicon atom that is used in stage b) of the process according to the invention may be a compound of silane, disilane, alkylsilane, alkoxysilane or siloxane type. Very preferably, said molecular compound has a composition of general formula $Si-(OR')_4$, where R' is an alkyl, aryl or acyl group, preferably an alkyl group, and very preferably an ethyl group. Said molecular compound that is used for the implementation of stage b) of the process according to the invention has a diameter that is greater than the maximum opening diameter of the pores of the zeolite and preferably comprises at most two silicon atoms per molecule. The molecular compound tetraethylorthosilicate (TEOS) of formula $Si(OCH_2CH_3)_4$, which has a diameter that is equal to 9.6 Å, is very advantageous for the implementation of stage b) of the process according to the invention. In particular, the TEOS is advantageous when it involves treating a MOR-structural-type zeolite that has a maximum pore opening diameter of 7 Å, an MFI-structural-type zeolite that has a maximum pore opening diameter of 5.6 Å, or an FER-structural-type zeolite that has a maximum pore opening diameter of 5.4 Å.

Said stage b) of the process according to the invention—which consists in treating the protonated zeolite, optionally subjected in advance to stage a), in the presence of at least one molecular compound that contains at least one silicon atom—is carried out by deposition of said compound on the outside surface of the zeolite. According to the invention, said stage b) is carried out by initiating the deposition of said molecular compound that contains at least one silicon atom in gaseous phase.

Stage b) according to the process of the invention is carried out in a fixed-bed reactor. Prior to the reaction of deposition in gaseous phase (CVD) in said fixed-bed reactor, the zeolite is preferably activated. The activation of the zeolite inside the fixed-bed reactor is carried out under oxygen, under air or under inert gas, or under a mixture of air and inert gas or oxygen and inert gas. The temperature for activating the zeolite is advantageously between 100 and 600° C., and very advantageously between 300 and 550° C. The molecular compound that contains at least one silicon atom that should be deposited on the outside surface of each of the crystals of the zeolite is sent into the vapor-phase reactor, whereby said molecular compound is diluted in a vector gas that may be either hydrogen ($H_2$), or air, or argon (Ar), or helium (He), or else nitrogen ($N_2$); preferably the vector gas is an inert gas that is selected from among Ar, He and $N_2$. Said molecular compound that contains at least one silicon atom is deposited on the outside surface of said zeolite in vapor phase, in the absence of any hydrocarbon compound. To obtain a layer of amorphous silica of optimal quality on the outside surface of the zeolite, it is necessary to select the operating conditions well for the deposition of the molecular compound that contains at least one silicon atom. In particular, the temperature of the zeolite bed during the deposition is preferably between 0 and 300° C., and very preferably between 50 and 200° C.; the partial pressure, in the gas phase, of the molecular compound to be deposited on the outside surface of the zeolite is preferably between 0.001 and 0.5 bar, and very preferably between 0.01 and 0.2 bar; the duration of the deposition is preferably between 10 minutes and 10 hours and very preferably between 30 minutes and 5 hours and even more preferably between 1 and 3 hours.

According to stage c) of the process according to the invention, the molecular compound that contains at least one silicon atom is decomposed by a heat treatment that is carried out at a temperature that is preferably between 200 and 700° C., more preferably between 300 and 500° C. Said heat treatment stage is implemented under air, under oxygen, under hydrogen, under nitrogen or under argon or under a mixture of nitrogen and argon. The duration of this treatment is advantageously between 1 and 5 hours. At the end of said heat treatment, a layer of amorphous silica is deposited on the outside surface of each of the crystals of the zeolite. According to the invention, the inside surface of each of the crystals of the zeolite is preferably lacking a deposition of a layer of amorphous silica. The maximum pore opening diameter of the modified zeolite, present in the catalyst that is prepared according to the process of the invention, is preferably unchanged relative to that of the initial zeolite that is not yet modified. Consequently, the modified zeolite that is contained in the catalyst that is prepared according to the process of the invention preferably has a maximum pore opening diameter that is less than or equal to 7 Å, and preferably less than 6.5 Å.

In the case where the substrate that is based on at least one protonated zeolite that is used for the implementation of stage a) of the process according to the invention consists of said protonated zeolite that is shaped with a matrix and optionally with a binder (second implementation of stage a)), the metal that is selected from among the metals of groups VIB and VIII can be introduced either virtually totally on the matrix, or partially on the zeolite and partially on the matrix, or preferably virtually totally on the zeolite, whereby this is carried out, in the manner that is known to one skilled in the art, by the suitable selection of parameters that are used during said deposition, such as, for example, the nature of the precursor of said metal.

In the case where the substrate that is based on at least one protonated zeolite that is used for the implementation of stage a) of the process according to the invention consists only of said protonated zeolite (first implementation of stage a)) whose characteristics in terms of maximum opening diameter of the pores, structure, and chemical composition are in accordance with what was said above in this description, the metal that is selected from among the metals of groups VIB and VIII is introduced directly into the protonated zeolite that comes preferably in the form of a powder. The shaping of the protonated zeolite with a matrix and optionally a binder is carried out during a stage d). Said stage d) for shaping may take place either directly after stage a) for introducing metal on the protonated zeolite and prior to the implementation of stages b) and c) of the process of the invention or after stages a), b) and c) of the process according to the invention or else after the implementation of said stages b) and c) and before the implementation of said stage a) when said stages b) and c) of the process according to the invention are carried out before stage a).

The matrix that is used for the shaping of the protonated zeolite—whereby said shaping is carried out either prior to stage a) of the process of the invention when the substrate that is based on said zeolite consists of said zeolite that is shaped with a matrix or during stage d) of the process according to the invention when the substrate that is based on said protonated zeolite consists only of said zeolite—is an amorphous or poorly-crystallized oxide-type porous mineral matrix. It is selected from among alumina, silica, silica-alumina, clays, in particular natural clays such as kaolin or bentonite, magnesia, titanium oxide, boron oxide, zirconia, aluminum phosphates, titanium phosphates, zirconium phosphates, and carbon. It is also possible to select a matrix from among the aluminates. Preferably, the matrix is an alumina under all its forms that are known to one skilled in the art, and preferably gamma-alumina. The shaping of said zeolite with at least one matrix is generally such that the catalyst comes in the form of cylindrical or multilobed—such as bilobed, trilobed, or multilobed—extrudates of straight or twisted shape, but it can optionally be such that the catalyst comes in the form of crushed powders, tablets, rings, balls, or wheels. The conditions of shaping the zeolite, the selection of the matrix, optionally the preliminary grinding of the zeolite, the peptization process, the addition of pore-forming agent, the mixing time, the extrusion pressure if the catalyst is put in extrudate form, the speed and the drying time are determined for each matrix according to the rules that are well known to one skilled in the art. The shaping of the zeolite with at least one matrix as described above can be carried out at various stages of the process according to the invention. More particularly, when the substrate that is based on said zeolite that is used during stage a) consists of said zeolite that is shaped with a matrix, the shaping is carried out prior to the implementation of stage a) of the process of the invention. When the substrate that is based on said zeolite that is used during stage a) consists only of said zeolite, the shaping is carried out either directly at the end of said stage a) and before the implementation of stages b) and c), or after the implementation of said stages b) and c) and before the implementation of said stage a) when said stages b) and c) precede said stage a), or else after the implementation of stages a), b) and c).

For example, one of the preferred methods for preparation of the catalyst according to the invention consists in exchanging a protonated zeolite with at least one metal that is selected from among the metals of groups VIB and VIII, preferably with nickel under its degree of oxidation +2. Said ionic exchange stage is followed by a stage for activation of the zeolite at a temperature of between 300 and 550° C., then the zeolite is treated at a temperature of between 50 and 200° C. in the presence of tetraethylorthosilicate (TEOS) that is deposited in vapor phase on the outside surface of said zeolite. The TEOS is decomposed by a heat treatment that is carried out in general at a temperature of between 300 and 500° C. under air. A modified zeolite is thus obtained under protonated form and comprising a layer of amorphous silica on its outside surface. Said modified zeolite is then shaped by extrusion by mixing it in a moist matrix gel (generally obtained by mixing at least one acid and one matrix powder), for example alumina, for a duration that is necessary for obtaining a good homogeneity of the paste thus obtained, for example for about ten minutes, then in passing said paste through a die to form extrudates, for example with a diameter of between 0.4 and 4 mm inclusive, preferably between 0.4 and 2.5 mm inclusive, and also preferably between 0.8 and 2.0 mm inclusive. The thus shaped extrudates then undergo drying for several hours at about 120° C. in a drying oven and a last stage of calcination, for example for about 2 hours at about 400° C. They generally consist of 10 to 90% by weight, preferably 30 to 80% by weight, of said modified zeolite, whereby the addition is formed by a matrix.

Another object of the invention is the use of the catalyst that is prepared according to the process of the invention and that comprises a modified zeolite in processes for chemical conversion of hydrocarbons and in particular in a process for oligomerization of an olefinic feedstock that contains hydrocarbon molecules that have 2 to 12 carbon atoms per molecule. Preferably, the feedstock that is used for the implementation of said process of oligomerization contains hydrocarbon molecules that contain 3 to 7 carbon atoms per molecule, and very preferably that contain 4 to 6 carbon atoms per molecule. The catalyst that is prepared according to the process of the invention is treated according to said stages a), b) and c) ex-situ: it is introduced into the reactor to carry out the oligomerization of hydrocarbon molecules that contain 3 to 7 carbon atoms per molecule once said stages a), b) and c) of the process for preparation of the catalyst according to the invention have been carried out. The feedstock that is used in the process for oligomerization according to the invention contains 20 to 100% by weight and preferably 25 to 80% by weight of olefins.

Possible sources for the olefinic feedstock that is used in the process for oligomerization of the invention are the light fraction of fluidized-bed cracking (fluid catalytic cracking, FCC), a steam-cracking device, and the effluents of etherification units.

Said oligomerization process is preferably implemented under the following operating conditions: the total pressure is between 0.1 and 10 MPa and preferably between 0.3 and 7 MPa; the temperature is between 40 and 600° C. and preferably between 100 and 400° C., the hourly volumetric flow rate (VVH) is between 0.01 and 100 $h^{-1}$ and preferably between 0.4 and 20 $h^{-1}$.

It is specified that, according to the invention, the oligomerization process corresponds to an addition that is limited to essentially 2 to 6 basic monomers or molecules, whereby said monomers are olefins.

The following examples illustrate this invention without limiting its scope.

EXAMPLES

Example 1 (Invention)

Preparation of a Catalyst that is Based on a Modified ZSM-5 Zeolite 40 g of H-ZSM-5 zeolite (Si/Al=45) is impregnated by ion exchange with a solution of 500 ml that contains 4.3 g/l of nickel sulfate. The ionic exchange is carried out for 24 hours at 80° C. After filtration and washing cycles, the zeolite that is thus exchanged with the nickel is dried for one night at 120° C. It is then introduced into a fixed-bed reactor where it is first subjected to activation under nitrogen flow at 450° C. The temperature of the reactor is then brought to 150° C., then a partial pressure of 0.15 bar of TEOS [Si $(OCH_2CH_3)_4$] is added in the nitrogen flow. After 2 hours of reaction, the zeolite is stripped for 2 hours at 150° C. to evacuate the TEOS that has not reacted. The decomposition of the TEOS is done under air at 450° C. for 3 hours. A modified Z1 zeolite in protonated form and of MFI-structural type and that comprises a layer of amorphous silica on its outside surface is thus obtained.

The Z1 zeolite is then shaped by extrusion with an alumina gel so as to obtain—after drying at 120° C. and calcination at 450° C. under dry air—a catalyst that contains 60% by weight of modified Z1 zeolite and 40% by weight of alumina.

Example 2 (Invention)

Preparation of a Catalyst that is Based on a Modified MOR Zeolite 40 g of H-MOR zeolite (Si/Al=55) is impregnated by ion exchange with a solution of 500 ml that contains 4.3 g/l of nickel sulfate. The ionic exchange is carried out for 24 hours at 80° C. After filtration and washing cycles, the zeolite that is thus exchanged with the nickel is dried for one night at 120° C. It is then introduced into a fixed-bed reactor where it is first subjected to activation under nitrogen flow at 450° C. The temperature of the reactor is then brought to 150° C., then a partial pressure of 0.15 bar of TEOS [Si $(OCH_2CH_3)_4$] is added into the nitrogen flow. After 2 hours of reaction, the zeolite is stripped for 2 hours at 150° C. to evacuate the TEOS that has not reacted. The decomposition of the TEOS is done under air at 450° C. for 3 hours. A modified Z2 zeolite in protonated form, of MOR-structural type, and that comprises a layer of amorphous silica on its outside surface is thus obtained.

The Z2 zeolite is then shaped by extrusion with an alumina gel in such a way as to obtain—after drying at 120° C. and calcination at 450° C. under dry air—a catalyst that contains 60% by weight of modified Z2 zeolite and 40% by weight of alumina.

Example 3 (Invention)

Preparation of a Catalyst that is Based on a Modified FER Zeolite 40 g of H-FER zeolite (Si/Al=26) is impregnated by ion exchange with a solution of 500 ml that contains 4.3 g/l of nickel sulfate. The ionic exchange is carried out for 24 hours at 80° C. After filtration and washing cycles, the zeolite that is thus exchanged with the nickel is dried for one night at 120° C. It is then introduced into a fixed-bed reactor where it is first subjected to activation under nitrogen flow at 450° C. The temperature of the reactor is then brought to 150° C., then a partial pressure of 0.15 bar of TEOS [Si $(OCH_2CH_3)_4$] is added into the nitrogen flow. After 2 hours of reaction, the zeolite is stripped for 2 hours at 150° C. to evacuate the TEOS that has not reacted. The decomposition of the TEOS is done under air at 450° C. for 3 hours. A modified Z3 zeolite in protonated form, of FER-structural type, and that comprises a layer of amorphous silica on its outside surface is thus obtained.

The Z3 zeolite is then shaped by extrusion with an alumina gel in such a way as to obtain—after drying at 120° C. and calcination at 450° C. under dry air—a catalyst that contains 60% by weight of modified Z3 zeolite and 40% by weight of alumina.

Example 4 (For Comparison)

Preparation of a Catalyst that is Based on a ZSM-5 Zeolite that is not Exchanged with a Metal 40 g of H-ZSM-5 zeolite (Si/Al=45) is introduced into a fixed-bed reactor where it is first subjected to activation under nitrogen flow at 450° C. The temperature of the reactor is then brought to 150° C., then a partial pressure of 0.15 bar of TEOS [Si [OCH$_2$CH$_3$)$_4$] is added into the nitrogen flow. After 2 hours of reaction, the zeolite is stripped for 2 hours at 150° C. to evacuate the TEOS that has not reacted. The decomposition of TEOS is done under air at 450° C. for 3 hours. A Z4 zeolite in protonated form, of MFI-structural type and that comprises a layer of amorphous silica on its outside surface is thus obtained.

The Z4 zeolite is then shaped by extrusion with an alumina gel in such a way as to obtain—after drying at 120° C. and calcination at 450° C. under dry air—a catalyst that contains 60% by weight of Z4 zeolite and 40% by weight of alumina.

Example 5 (For Comparison)

Preparation of a Catalyst that is Based on an MOR Zeolite that is not Exchanged with a Metal 40 g of H-MOR zeolite (Si/Al=55) is introduced into a fixed-bed reactor where it is first subjected to activation under nitrogen flow at 450° C. The temperature of the reactor is then brought to 150° C., then a partial pressure of 0.15 bar of TEOS [Si (OCH$_2$CH$_3$)$_4$] is added into the nitrogen flow. After 2 hours of reaction, the zeolite is stripped for 2 hours at 150° C. to evacuate the TEOS that has not reacted. The decomposition of the TEOS is done under air at 450° C. for 3 hours. A Z5 zeolite in protonated form, of MOR-structural type and that comprises a layer of amorphous silica on its outside surface is thus obtained.

The Z5 zeolite is then shaped by extrusion with an alumina gel in such a way as to obtain—after drying at 120° C. and calcination at 450° C. under dry air—a catalyst that contains 60% by weight of Z5 zeolite and 40% by weight of alumina.

Example 6 (For Comparison)

Preparation of a Catalyst that is Based on an FER Zeolite that is not Exchanged with a Metal 40 g of H-FER zeolite (Si/Al=26) is introduced into a fixed-bed reactor where it is first subjected to activation under nitrogen flow at 450° C. The temperature of the reactor is then brought to 150° C., then a partial pressure of 0.15 bar of TEOS [Si (OCH$_2$CH$_3$)$_4$] is added into the nitrogen flow. After 2 hours of reaction, the zeolite is stripped for 2 hours at 150° C. to evacuate the TEOS that has not reacted. The decomposition of the TEOS is done under air at 450° C. for 3 hours. A Z6 zeolite in protonated form, of FER-structural type and that comprises a layer of amorphous silica on its outside surface is thus obtained.

The Z6 zeolite is then shaped by extrusion with an alumina gel in such a way as to obtain—after drying at 120° C. and calcination at 450° C. under dry air—a catalyst that contains 60% by weight of Z6 zeolite and 40% by weight of alumina.

Example 7 (Invention)

Preparation of a Catalyst that is Based on a Modified MFI Zeolite 40 g of H-ZSM-5 zeolite (Si/Al=45) is impregnated by ion exchange with a solution of 500 ml that contains 20 g/l of chromium acetate. The ionic exchange is carried out for 24 hours at 70° C. After filtration and washing cycles, the zeolite that is thus exchanged with the chromium is dried for one night at 120° C., then calcined for 2 hours under air at 550° C. It is then introduced into a fixed-bed reactor where it is first subjected to activation under nitrogen flow at 450° C. The temperature of the reactor is then brought to 150° C., then a partial pressure of 0.15 bar of TEOS [Si (OCH$_2$CH$_3$)$_4$] is added into the nitrogen flow. After 2 hours of reaction, the zeolite is stripped for 2 hours at 150° C. to evacuate the TEOS that has not reacted. The decomposition of the TEOS is done under air at 450° C. for 3 hours. A modified Z7 zeolite in protonated form, of MFI-structural type and that comprises a layer of amorphous silica on its outside surface is thus obtained.

The Z7 zeolite is then shaped by extrusion with an alumina gel in such a way as to obtain—after drying at 120° C. and calcination at 450° C. under dry air—a catalyst that contains 60% by weight of modified Z7 zeolite and 40% by weight of alumina.

Example 8

Catalytic Evaluation of Catalysts that are Based on Modified Z1, Z2, Z3 and Z7 Zeolites and Based on Z4, Z5 and Z6 Zeolites for Oligomerization of Light Olefins The performance levels of the catalysts that are prepared according to Examples 1 to 7 above have been evaluated in the reaction for oligomerization of a light olefinic fraction that contains 58% of C4 olefins in a paraffin mixture.

The operating conditions of the tests are as follows:
Temperature: 230° C.
Pressure: 6 MPa
VVH (h$^{-1}$) [volume of catalyst/volumetric flow rate of the feedstock]: 1 h$^{-1}$ The catalysts are activated in situ in advance under N$_2$ at 450° C. for 2 hours.

The performance levels of the catalysts that are based on the MFI-structural-type zeolite are provided in Table 1.

TABLE 1

Performance Levels of the Catalysts that are Based on the MFI Zeolite.

|  | Catalyst Based on Z1 (Invention) | Catalyst Based on Z4 (For Comparison) | Catalyst Based on Z27 (Invention) |
|---|---|---|---|
| C4 Olefinic Conversion (%) | 99 | 99 | 99 |
| Gasoline Fraction Yield (%) | 55 | 60 | 52 |
| Diesel Fraction Yield (%) | 45 | 40 | 48 |
| Cetane Number | 46.7 | 44.6 | 46.5 |

The performance levels of the catalysts that are based on the FER-structural-type zeolite are provided in Table 2.

TABLE 2

Performance Levels of the Catalysts that are Based on the FER Zeolite.

| | Catalyst Based on Z3 (Invention) | Catalyst Based on Z6 (For Comparison) |
|---|---|---|
| C4 Olefinic Conversion (%) | 85 | 85 |
| Gasoline Fraction Yield (%) | 60 | 61 |
| Diesel Fraction Yield (%) | 40 | 39 |
| Cetane Number | 39.2 | 36.2 |

The performance levels of the catalysts that are based on MOR-structural-type zeolite are provided in Table 3.

TABLE 3

Performance Levels of the Catalysts that are Based on the MOR Zeolite.

| | Catalyst Based on Z2 | Catalyst Based on Z5 |
|---|---|---|
| C4 Olefinic Conversion (%) | 99 | 99 |
| Gasoline Fraction Yield (%) | 42 | 44 |
| Diesel Fraction Yield (%) | 58 | 56 |
| Cetane Number | 42.4 | 39.3 |

The catalytic performance levels that are presented in Tables 1, 2 and 3 demonstrate that the catalysts that comprise a modified zeolite and that are prepared according to the process of the invention make it possible to increase in particular the diesel fraction yield when they are tested in a reaction for oligomerization of light olefins. The quality of this gas oil, measured by its cetane number (IC), is also improved relative to the one that is presented by a diesel fraction that is obtained by means of a catalyst that comprises a zeolite that has not been modified according to the process of the invention.

The invention claimed is:

1. In a catalytic process for oligomerization of an olefinic feedstock containing hydrocarbon molecules having 2 to 12 carbon atoms per molecule, the improvement wherein the catalyst contains at least one modified zeolite, whereby said zeolite—before being modified—has a maximum pore opening diameter that is less than or equal to 7 Å, said catalyst being that prepared by a process comprising:
   a) at least one stage for introducing at least one metal that is selected from among the metals of groups VIB and VIII of the periodic table on a substrate comprising at least one protonated zeolite of a structural type selected from the group consisting of MEL, MFI, IT, NES, EUO, ERI, FER, CHA, MFS, MWW, MTT, TON and MOR, said at least one protonated zeolite being the only zeolite in the catalyst,
   b) at least one stage for treating said zeolite in the presence of at least one molecular compound that contains at least one silicon atom, said molecular compound having a molecular diameter that is greater than the maximum opening diameter of the pores of said zeolite, said treating comprising depositing said molecular compound on the outside surface of said zeolite in gaseous phase, and
   c) at least one heat treatment stage to form a layer of amorphous silica on the outside surface of the zeolite.

2. A process according to claim 1, wherein said oligomerization process is implemented at a temperature of between 40 and 600° C., with a total pressure of between 0.1 and 10 MPa and an hourly volumetric flow rate (VVH) of between 0.01 and 100 h$^{-1}$.

3. An oligomerization process according to claim 1, wherein said at least one metal that is selected from among the metals of groups VIB and VIII of the periodic table is nickel, iron, palladium, ruthenium or chromium.

4. An oligomerization process according to claim 1, wherein said zeolite is an MFI-, MOR- or FER-structural-type zeolite.

5. An oligomerization process according to claim 1, wherein said molecular compound has a composition of general formula Si—(OR')$_4$ where R' is an alkyl, aryl or acyl group.

6. An oligomerization process according to claim 1, wherein said zeolite is FER- or -—MF1-structural type zeolite.

7. An oligomerization according to claim 1, wherein said zeolite contains, before being modified, silicon and aluminum in a proportion such that the Si/Al atomic ratio is between 2 and 200.

8. An oligomerization process according to claim 1, wherein said at least one metal that is selected from among the metals of groups VIB and VIII of the periodic table is nickel, iron, palladium, ruthenium or chromium.

9. An oligomerization process according to claim 1, wherein said molecular compound that contains at least one silicon atom is selected from among compounds of formulas Si—R$_4$ and Si$_2$—R$_6$ wherein R is hydrogen or an alkyl, aryl or acyl group, or an alkoxy group (O—R') or a hydroxyl group (—OH) or a halogen, wherein R is identical or different.

10. An oligomerization process according to claim 1, wherein said molecular compound has a composition of general formula Si—(OR')$_4$ where R' is an alkyl, aryl or acyl group.

11. An oligomerization process according to claim 1, wherein said stage b) is carried out by initiating the deposition of said molecular compound that contains at least one silicon atom in gaseous phase.

12. An oligomerization process according to claim 1, wherein said stage b) is carried out in a fixed-bed reactor.

* * * * *